United States Patent [19]
McDonough et al.

[11] Patent Number: 5,431,884
[45] Date of Patent: Jul. 11, 1995

[54] SPECIMEN TRANSPORTING AND PROCESSING SYSTEM

[75] Inventors: David McDonough, Crystal Lake; Janet Ratajczak, McHenry; Lawrence G. Ponsi, Wheeling; John J. Newton, Palatine, all of Ill.

[73] Assignee: Sage Products, Inc., Crystal Lake, Ill.

[21] Appl. No.: 200,205

[22] Filed: Feb. 22, 1994

[51] Int. Cl.⁶ .............................. B01L 11/00
[52] U.S. Cl. ...................... 422/101; 422/61; 422/102; 73/64.56; 73/864.41; 73/864.91; 209/17
[58] Field of Search ........ 422/101, 102, 61; 436/66, 177, 178; 209/17; 73/864.41, 64.56, 864.91; 128/757, 304, 305

[56] References Cited
U.S. PATENT DOCUMENTS 4,859,610 8/1989 Maggio .................. 436/518
5,149,506 9/1992 Skiba et al. ............. 422/102

*Primary Examiner*—David A. Redding
*Attorney, Agent, or Firm*—Lee, Mann, Smith, McWilliams, Sweeney & Ohlson

[57] ABSTRACT

A system for transporting and processing a specimen, and an assembly employing that system. The transporting and processing system comprises a tubular container having a filter assembly removably secured within the container by a threaded collar. A cap is applied to the collar, and a spoon is secured to the underside of the cap for collecting a specimen and inserting it within the filter contained within the container. The spoon is shaped to fit within the filter when the cap is applied. In the assembly, the specimen transporting and processing system is utilized along with a separate container having a spoon assembly and cap, but no filter assembly. A stand is provided for retaining both containers.

20 Claims, 1 Drawing Sheet

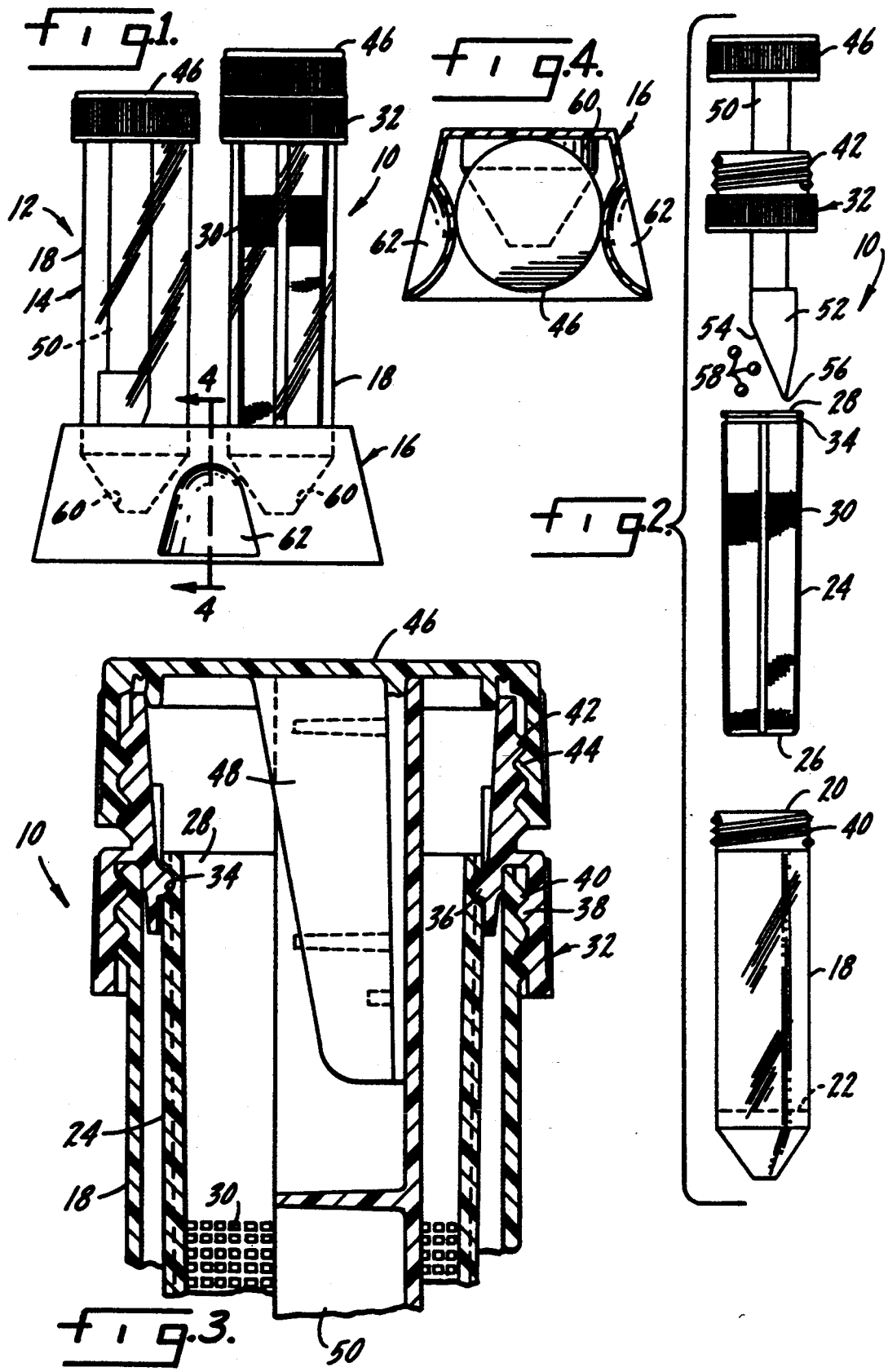

SPECIMEN TRANSPORTING AND PROCESSING SYSTEM

BACKGROUND OF THE INVENTION

This invention relates to collection of specimens, and more particularly to the collection, transporting and processing of a stool sample where the specimen typically is collected by the patient for later diagnostic work.

Stool sampling is an important facet of modern health care. Samples are obtained and processed in many different manners, but with the great concern for the safety of the diagnostician and physician, secure yet easy-to-use systems are imperative.

Typical specimen collecting systems comprise, in their crudest form, simply a container and a lid. More typically, however, such systems include a container and lid, some means for collecting the sample, such as a small spoon or spatula, and a liquid reagent provided within the container for mixing with the stool sample. The patient collects a sample, inserts the sample into the container, and then delivers the container to an appropriate person for immediate processing in a laboratory. When a liquid reagent is used, commonly the container is shaken in an effort to mix the liquid and the stool sample, often after the spoon has been first employed to begin such mixture.

Such prior art devices, while being effective collection devices, are poor means of mixing the liquid reagent with the sample taken. If the spoon is used for mixing purposes, only a partial mix is obtained, and the diagnostician must then carefully remove a desired amount for processing. If shaking is employed, often the admixture is equally as incomplete. Also, solids which form no part of the desired diagnostic procedure remain, and must be removed in order to avoid interference with testing.

SUMMARY OF THE INVENTION

The present invention is an improvement over prior art devices, and relates to a specimen transporting and processing system which provides ease of collection and processing. The system comprises a tubular container having an open end. A tubular filter assembly is provided, the filter assembly being shaped to fit within the container through the open end. The filter assembly has an open mouth at one end and a closed opposite end. Means is provided for attachment of the filter assembly to the container at the open end of the container. Means is also provided within the filter assembly for agitation of a specimen inserted therewithin. Finally, is provided for sealing the container at the open end.

In accordance with the preferred form of the invention, the attachment means for attaching the filter assembly to the tubular container comprises a collar shaped to engage the open end of the container. The collar has an internal filter retainer shaped to grip the filter. The filter assembly contains an annular groove at the open mouth, and the filter retainer comprises an annular protrusion shaped to engage the groove. Preferably, the container and the collar are threaded for easy inter-engagement.

The sealing means comprises a cap shaped to be retained on the collar. Preferably, both the cap and the collar are threaded for inter-engagement in order to seal the container. A specimen sampling implement is secured to the underside of the cap and shaped to be inserted through the open mouth through the assembly when the container is closed. Preferably, the specimen sampling implement comprises a spoon.

The filter assembly includes a perforated wall. For agitation of a sample inserted within the filter assembly, the agitation means comprises at least one loose mixing ball within the filter assembly. Also, for diagnostic purposes, it is preferred that a liquid reagent be contained within the tubular container so that initial mixing can be performed by the patient immediately after collection of a specimen.

A specimen transporting, sampling and processing assembly is composed of the specimen transporting and processing system, along with a separate tubular container and cap. The separate container includes a sampling spoon secured to the underside of the cap, as well. Both containers may be mounted in a holder in order to retain the containers in an upright orientation. The holder includes a pair of cavities, each of the cavities being shaped to retain one of the tubular containers.

BRIEF DESCRIPTION OF THE DRAWINGS

The invention is described in greater detail in the following description of an example embodying the best mode of the invention, taken in conjunction with the drawing figures, in which:

FIG. 1 is an elevational view of a specimen transporting, sampling and processing assembly according to the invention, FIG. 2 is an exploded view of a specimen transporting and processing system according to the invention, which is also shown as the right-hand container in FIG. 1, when fully assembled, FIG. 3 is an enlarged, cross-sectional view of the top portion of the specimen transporting and processing system according to the invention, illustrating details of assembly, and FIG. 4 is an enlarged cross section taken along lines 4—4 of FIG. 1 and showing mounting of an auxiliary cap.

DESCRIPTION OF AN EXAMPLE EMBODYING THE BEST MODE OF THE INVENTION

A specimen transporting and processing system according to the invention is shown generally at 10 in the drawing figures. The specimen transporting and processing system 10 can be used alone, or can be part of a specimen transporting, sampling and processing assembly as shown at 12 in FIG. 1, where the system 10 and a second container 14 are provided in a holder 16 which retains the two containers in an upright orientation.

The specimen transporting and processing system 10 is composed of several elements. First is a tubular container 18 having an open end 20. If a liquid reagent is employed as part of the system 10, a quantity of liquid reagent, shown generally at 22, is held within the container 18.

A tubular filter assembly 24 is provided, the assembly 24 being shaped to fit within the container 18 when the system 10 is fully assembled. The assembly 24 has a closed bottom 26 and an open mouth 28 at its top. The wall of the filter assembly 24 is generally perforated, as shown by the perforations 30.

The filter assembly 24 is attached to the container 18 by means of a collar 32. As best shown in FIG. 3, the filter assembly 24 includes an external annual groove 34 proximate the open mouth 28. For retaining the filter assembly 24 within the collar 32, the collar 32 includes a filter retainer in the form of an annular protrusion 36 shaped to engage the groove 34. Therefore, the collar 32 and filter assembly 24 normally are snapped together as a unit with the protrusion 36 engaged in the groove 34.

The collar 32 includes an internal female thread 38 shaped to engage a corresponding male thread 40 formed at the top of the tubular container 18 adjacent the open end 20. Thus, the collar 32 is threadedly secured to the tubular container 18, although other means of securement can be employed, if desired, and further sealing rings (not illustrated) can be employed. Whatever the type of securing mechanism utilized, the interface between the collar 32 and the tubular container 18 is preferably liquid-tight.

The collar 32 also includes a male thread 42 at the top thereof which engages a corresponding female thread 44 formed in a cap 46. When the cap 46 is applied to the collar 32, the system 10 is sealed.

An integral support 48 extends downwardly from the underside of the cap 46. A specimen sampling implement in the form of spoon 50 may be secured to the support 48 by appropriate means, such as by force fitting, an adhesive, sonic welding, heat staking, or otherwise. The spoon 50 has a scoop 52 open at 54 and including a straight cutting edge 56 for facilitating scooping of a specimen.

Proper mixing of the specimen with the liquid reagent 22, if employed, is an important feature of the invention. For agitation purposes, one or more loose mixing balls 58 are provided, and are located within the filter assembly 24, when the system 10 is fully assembled. The mixing balls 58 are of appropriate material and size to mix the specimen and the liquid reagent 22 when the system 10 is shaken after a specimen is inserted therewithin. If desired, one or more mixing ball 58 can also be employed in the container 18 as well as within the filter assembly 24.

As explained above, the system 10 can be used alone, or as one element of the specimen transporting, sampling and processing assembly 12. The second container 14 of the assembly 12 preferably is comprised of a tubular container 18 and cap 46 applied thereon, with the spoon 50 secured beneath the cap 46 as explained above. Thus, the filter assembly 24, collar 32 and mixing balls 58 are normally not employed as part of the second container 14. On occasion, the mixing balls 58 may, however, be employed in the second container 14.

The system 10 and second container 14 are seated within the holder 16. The holder 16 includes a pair of cavities 60 shaped to accommodate the two containers. Preferably, the holder 16 is thermoformed or blow molded from plastic, although it can be made from other materials and formed in any conventional fashion. The holder 16 can also include opposite detents 62, as shown, for capturing an auxiliary cap 46 underneath the holder, as best shown in FIG. 4. The cap 46 is snapped in place between the detents 62 and the cavities 60.

In use, the system 10 is provided to the patient in a fully assembled fashion as shown in FIGS. 1 and 3. Normally, the liquid reagent 22 is also contained therewithin. The patient unscrews the cap 46 from the collar 32, removing the cap 46 and spoon 50 for collection of a specimen. After the specimen has been collected in the scoop 52, the cap 46 and spoon 50, carrying the specimen, are reinserted and the system 10 is reassembled as shown in FIGS. 1 and 3. The system 10 is then shaken, with the mixing balls 58 agitating the specimen and liquid reagent during shaking. Liquified portions of the specimens are then free to pass through the perforations 30 of the filter assembly 24. For later processing, the collar 32 can be removed with the cap 46 thereon, leaving only the container 18 and the liquified specimen therewithin. The container 18 can then be centrifuged or otherwise handled during later diagnostic processes.

The second container 14 is also used for specimen collection, but the filter assembly 24, and retaining collar 32, are not employed. Both containers 14 and 18 can therefore be employed to collect specimens for different diagnostic processes.

Various changes can be made to the invention without departing from the spirit thereof or scope of the following claims.

What is claimed is:

1. A specimen transporting and processing system, comprising:
   a. a tubular container having an open end,
   b. a tubular filter assembly shaped to fit within said container through said open end, said filter assembly having an open mouth at one end and a closed opposite end and a tubular body between said ends,
   c. means for attachment of said filter assembly to said container at said open end,
   d. moveable means located within said tubular body for agitation of a specimen inserted therewithin, and
   e. means for sealing said container at said open end.

2. A specimen transporting and processing system according to claim 1 in which said attachment means comprises a collar shaped to engage said open end, said collar having an internal filter retainer for gripping said filter assembly.

3. A specimen transporting and processing system according to claim 1 in which said filter assembly includes an annular groove at said open mouth, and said filter retainer comprises an annular protrusion shaped to engage said groove.

4. A specimen transporting and processing system according to claim 2 in which said container includes first attachment threads at said open end and said collar includes complementary second attachment threads engageable with said first attachment threads.

5. A specimen transporting and processing system according to claim 1 in which said attachment means comprises a collar engaged on said open end, and said sealing means comprises a cap formed to be retained on said collar.

6. A specimen transporting and processing system according to claim 5 in which said collar includes first attachment threads and said cap includes complementary second attachment threads engageable with said first attachment threads.

7. A specimen transporting and processing system according to claim 1 in which said movable means comprises at least one loose mixing ball within said tubular body.

8. A specimen transporting and processing system according to claim 1 in which said sealing means comprises a cap, and including a specimen sampling implement secured to said cap and shaped to be inserted through said open mouth into said filter assembly.

9. A specimen transporting and processing system according to claim 8 in which said specimen sampling implement comprises a spoon.

10. A specimen transporting and processing system according to claim 1 in which said tubular body includes a perforated wall.

11. A specimen transporting and processing system, comprising:
   a. a tubular container having an open end,
   b. a tubular filter assembly shaped to fit within said container through said open end, said filter assembly having an open mouth at one end and a closed opposite end and a tubular body between said ends,
   c. a threaded collar for removable attachment of said filter assembly to said container at said open end,
   d. movable means located within said tubular body for agitation of a specimen inserted therewithin, and
   e. a cap shaped to engage said collar for sealing said container at said open end,
   f. a specimen sampling implement secured to said cap and shaped to be inserted through said open mouth into said filter assembly, and
   g. a liquid reagent in said tubular container.

12. A specimen transporting and processing system according to claim 11 in which said filter assembly includes an annular groove at said open mouth and said collar includes an internal annular protrusion shaped to engage said groove.

13. A specimen transporting and processing system according to claim 11 in which said movable means comprises at least one loose mixing ball within said tubular body.

14. A specimen transporting and processing system according to claim 11 in which said specimen sampling implement comprises a spoon.

15. A specimen transporting, sampling and processing assembly comprising:
   a. a first receptacle, comprising:
      i. a tubular first container having an open end,
      ii. a tubular filter assembly shaped to fit within said first container through said open end, said filter assembly having an open mouth at one end and a closed opposite end,
      iii. means for attachment of said filter assembly to said first container at said open end,
      iv. means within said filter assembly for agitation of a specimen inserted therewithin, and
      v. means for sealing said first container at said open end,
   b. a second receptacle, comprising:
      i. a tubular second container having an open end, and
      ii. means for sealing said second container at said open end, and
   c. a holder including means for retaining said receptacles in an upright orientation.

16. An assembly according to claim 15 in which said attachment means comprises a collar shaped to engage said open end, said collar having an internal filter retainer for gripping said filter.

17. An assembly according to claim 16 in which said filter assembly includes an annular groove at said open mouth, and said filter retainer comprises an annular protrusion shaped to engage said groove.

18. An assembly according to claim 15 in which said specimen sampling implement comprises a spoon.

19. An assembly according to claim 15 in which each sealing means comprises a cap, and including a specimen sampling implement secured to said cap and shaped to be inserted through said open mouth into said filter assembly.

20. An assembly according to claim 15 in which said means for retaining comprises a pair of cavities in said holder, each cavity being shaped to engage one of said containers.

* * * * *